(12) United States Patent  (10) Patent No.: US 8,159,348 B2
Ellis  (45) Date of Patent: Apr. 17, 2012

(54) COMMUNICATION SYSTEM WITH ANTENNA BOX AMPLIFIER

(75) Inventor: Michael G. Ellis, Alpharetta, GA (US)

(73) Assignee: CardioMEMS, Inc., Atlanta, GA (US)

( * ) Notice: Subject to any disclaimer, the term of this patent is extended or adjusted under 35 U.S.C. 154(b) by 648 days.

(21) Appl. No.: 12/393,206

(22) Filed: Feb. 26, 2009

(65) Prior Publication Data

US 2009/0237213 A1    Sep. 24, 2009

Related U.S. Application Data

(60) Provisional application No. 61/032,569, filed on Feb. 29, 2008.

(51) Int. Cl.
*G08B 13/14* (2006.01)

(52) U.S. Cl. ............... 340/572.1; 340/10.1; 343/700 R; 600/300

(58) Field of Classification Search .... 340/572.1–572.8, 340/10.1; 343/700 R, 718, 904; 600/300, 600/301
See application file for complete search history.

(56) References Cited

U.S. PATENT DOCUMENTS

| | | | |
|---|---|---|---|
| 5,626,630 A | 5/1997 | Markowitz et al. | |
| 6,111,520 A * | 8/2000 | Allen et al. | 340/870.16 |
| 7,060,030 B2 * | 6/2006 | Von Arx et al. | 600/300 |
| 7,245,117 B1 | 7/2007 | Joy et al. | |
| 7,471,986 B2 * | 12/2008 | Hatlestad | 607/61 |
| 7,686,768 B2 * | 3/2010 | Bodecker et al. | 600/486 |
| 2009/0248112 A1 * | 10/2009 | Mumbru et al. | 607/60 |

FOREIGN PATENT DOCUMENTS

JP    60229536    11/1985

OTHER PUBLICATIONS

International Search Report and Written Opinion, PCT/US09/035224, mailed Jun. 29, 2009.

* cited by examiner

*Primary Examiner* — Eric M Blount
(74) *Attorney, Agent, or Firm* — Kilpatrick Townsend & Stockton LLP

(57) ABSTRACT

A communication system for communicating with an implanted wireless sensor is provided. A transmit antenna element can propagate an energizing signal onto a communication medium and a receive antenna element can recover a responsive implanted sensor response signal. The antenna box includes a power amplifier for amplifying the energizing signal and timing regeneration circuitry for detecting an end to signals and outputting control signals for selecting mode operation. The antenna box can receive the energizing signal from the antenna cable in a transmit mode and provide the implanted sensor response signal to the antenna cable in a receive mode. The antenna box can communicate with an electronic box and/or conversion box that provide and receive signals and provide power via the antenna cable.

20 Claims, 16 Drawing Sheets

COMMUNICATION SYSTEM WITH ANTENNA BOX AMPLIFIER

CROSS-REFERENCE TO RELATED APPLICATIONS

This application claims priority to U.S. Provisional Patent Application No. 61/032,569, filed Feb. 29, 2008 and entitled "Communication System with Antenna Box Amplifier," the entirety of which is hereby incorporated by reference.

FIELD OF THE INVENTION

The present invention generally relates to wireless communication systems, and in particular to antenna systems for communicating with an implanted wireless sensor.

BACKGROUND

Wireless sensors can be implanted within the body and used to monitor physical conditions, such as pressure or temperature. For example, U.S. Pat. No. 6,111,520 and U.S. Pat. No. 7,245,117 describe wireless sensors that can be implanted within the body and certain techniques that can be employed to communicate with the wireless sensors. These sensors can be used to monitor physical conditions within the heart or an abdominal aneurysm. An abdominal aortic aneurysm (AAA) is a dilatation and weakening of the abdominal aorta that can lead to aortic rupture and sudden death. In the case of a repaired abdominal aneurysm, a sensor can be used to monitor pressure within the aneurysm sac to determine whether the intervention is leaking. In the case of chronic heart failure, a pressure sensor, implanted in the right ventricle of the heart, can provide warning signs, in some cases up to five days in advance, before the patient experiences any external symptoms.

Typically, the implanted sensors utilize an inductive-capacitive ("LC") resonant circuit with a variable capacitor. The capacitance of the circuit may vary with the pressure of the environment in which the sensor is located and thus, the resonant frequency of the circuit may vary as the pressure varies. The resonant frequency of the circuit can be tracked and used to calculate systolic, diastolic, and mean pressure. The resonant frequency can be obtained, or otherwise monitored, wirelessly using an antenna to obtain signals from the LC circuit. In some systems, an electronic system sends signals to the antenna for transmission to the LC circuit to energize or otherwise excite the LC circuit. The LC circuit responds with a signal that is received by the antenna and provided to the electronic system for analysis.

The electronic box, or system, is connected to the antenna by an antenna cable and, optionally, an antenna box or board that includes electronics used to operate the antenna. The cable may be a custom multi-wire cable assembly that includes different individual cables, each carrying a signal between the electronic box and the antenna. Signals carried by the multi-wire cable can include three power signals, a ground signal, a differential transmit gate signal, a differential receive gate signal, a transmit signal, and a receive signal. The three power signals can include a first positive voltage supplying power to the antenna box electronics, a second positive voltage supplying power for low voltage electronics in the antenna box, and a negative voltage supplying power for the low voltage electronics in the antenna box. The differential transmit gate signals are control signals for the transmitter functions in the antenna box electronics. The differential receive gate signals are control signals for the receiver functions in the antenna box electronics. The transmit signal is a signal that is transmitted by the antenna. The receive signal is a signal from the LC circuit that is received by the antenna. In some systems, the antenna cable may include ten different cables, such as two coaxial cables for the transmit and receive signals and eight single line wires for other signals, to provide the signals needed to control, power, and otherwise permit the antenna and the antenna box electronics to operate.

A multi-wire antenna cable system that includes ten different cables may be useful in some circumstances. FIGS. 1 and 2 illustrate an example of an antenna 10 that can be connected to an electronic box (not shown) via a relatively thick cable 12. The cable 12 may include multiple wires for carrying various types of signals between the antenna 10 and electronic box. For example, the cable 12 can carry transmitted signals from the electronic box, received signals from an implanted sensor, timing signals to control electronics associated with the antenna, and power to the circuitry in the antenna box. Each wire may carry one type of signal and the cable 12 may include ten to twelve, or more, different wires to provide such capacity. In some circumstances, the multi-wire antenna cable 12 may limit movement of the antenna 10 or antenna positioning—preventing the antenna 10 from being placed in an optimal position for obtaining signals from the LC circuit. Accordingly, a need exists for an antenna with increased placement flexibility for wirelessly communicating with an implanted sensor.

SUMMARY

In an embodiment, a communication system for communicating with an implanted wireless sensor is provided. The system includes a transmit antenna element, receive antenna element, and an antenna box. The transmit antenna element can propagate an energizing signal onto a communication medium. The receive antenna element can recover an implanted sensor response signal from the communication medium. The implanted sensor response signal is responsive to the energizing signal.

The antenna box is in electrical communication with the transmit antenna element and the receive antenna element and includes a power amplifier and timing regeneration circuitry. The power amplifier can amplify the energizing signal received from an antenna cable to a second power level from a first power level and can provide the energizing signal at the second power level to the transmit antenna element. The timing regeneration circuitry can output control signals to change the antenna box to a receive mode upon detecting an end to the energizing signal and to change the antenna box to a transmit mode upon identifying an end to the implanted sensor response signal by identifying an end to a response time window of a pre-set amount of time. The antenna box can receive the energizing signal from the antenna cable in the transmit mode and provide the implanted sensor response signal to the antenna cable in the receive mode.

In some embodiments, the antenna box is in electrical communication with an electronic box and/or conversion box through the antenna cable.

These illustrative embodiments are mentioned not to limit or define the invention, but to provide examples to aid understanding thereof. Other aspects, advantages, and features of the present invention will become apparent after review of the entire application, including the following sections: Brief Description of the Drawings, Detailed Description, and Claims.

DETAILED DESCRIPTION

Figure 1:
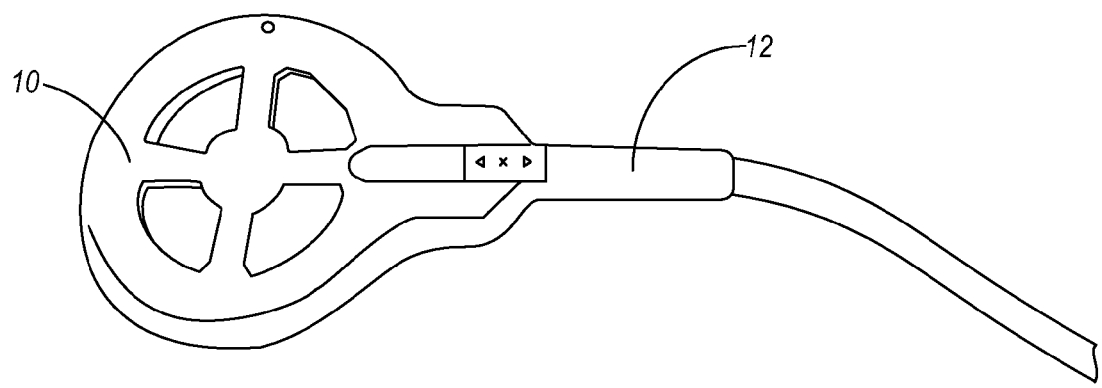
FIG. 1 illustrates an antenna with a relatively thick cable.
Figure 2:
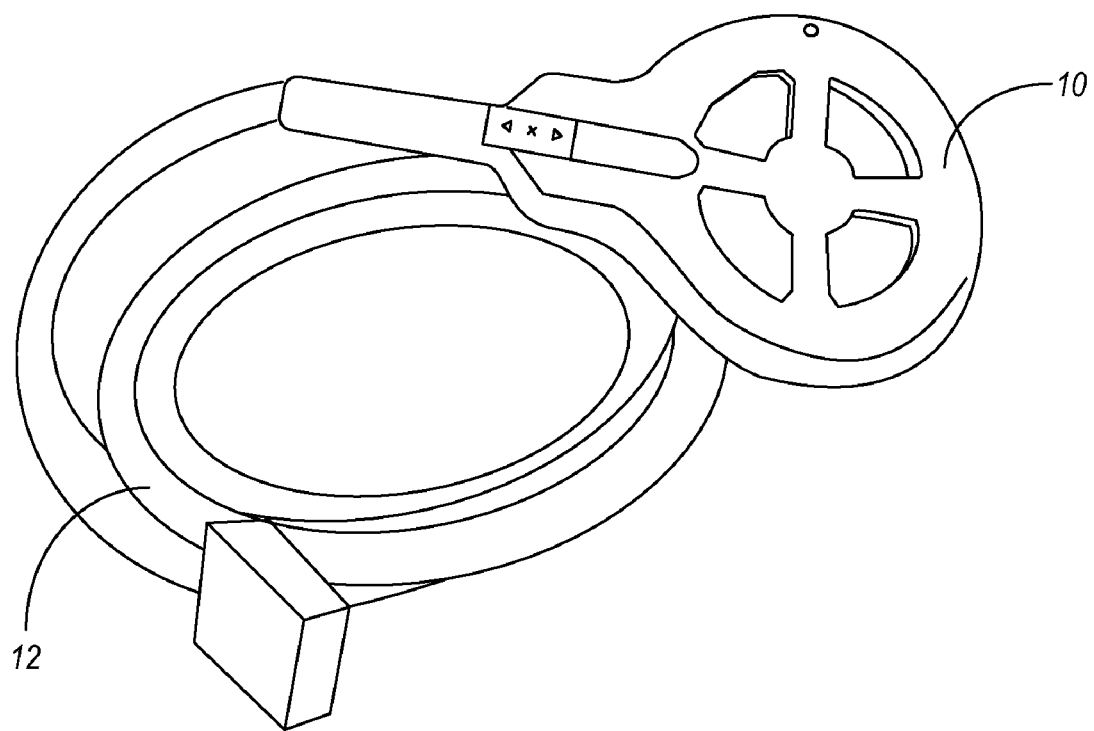
FIG. 2 is a perspective view of the antenna of FIG. 1 in a different position and with additional elements.

Certain aspects and embodiments of the present invention relate to methods and systems for communicating with an implanted wireless sensor using an antenna and antenna cable that provide for increased placement flexibility. In some embodiments, communication systems and methods may be used with implanted sensors to monitor qualitative measurements, such as blood pressure, for an abdominal aneurysm or for chronic heart failure. Some disclosed methods and systems provide an antenna box that is adapted to communicate with an electronic box via a single cable. Additional cables, however, may be utilized in some embodiments to connect the antenna box and the electronic box. The antenna box according to some embodiments can include a radio frequency (RF) power amplifier that provides amplification to energizing signals and supports signal transmission to an implanted wireless sensor. Examples of an RF power amplifier include a push-pull amplifier, modified H-bridge amplifier, and a full H-bridge amplifier. The electronic box according to some embodiments can include, or be connected to, a conversion box adapted to support communication using a single cable and to provide an interface between an electronic box and the antenna box. For example, a conversion box may be connected between an existing electronic box and an antenna box to provide an option of connecting the antenna box using a single wire or cable.

The term "box" as used herein refers to a component or a collection of components that can perform certain functions and does not necessarily refer to a physical housing for the component or collection of components. One example is an electronic box that is included in the same housing as a conversion box. A second example is that one component of the electronic box may be included in a first housing and another component of the electronic box may be included in a second, separate, housing.

In some embodiments, the electronic box generates an RF signal, such as an energizing signal, for transmission to an implanted sensor via the antenna box and an antenna. The energizing signal may be a low power RF signal having a certain duration and that is provided to a conversion box. The conversion box may be adapted to add a DC power signal to the energizing signal and, in some embodiments, attenuate the energizing signal to a pre-set level. The power signal may be electrical energy at a pre-set voltage level. The conversion box can be connected to a cable, such as a coaxial cable, that is also connected to the antenna box. In some embodiments, the cable is a single coaxial cable. In other embodiments, the cable is a bundled cable. The conversion box may be adapted to transmit the combined energizing signal and power signal to the antenna box.

The antenna box can receive the combined energizing signal and power signal and use the power signal to provide electric power to the antenna box circuitry. In some embodiments, the antenna box includes a voltage regulator that is adapted to convert the voltage level of the power signal into one or more different voltage levels. The energizing signal can be amplified by a power amplifier and transmitted via the antenna to an implanted sensor. The implanted sensor can return a response signal that is detected by the antenna and received by the antenna box. An end to the response signal can be identified by identifying an end to a response time window of a pre-set amount of time. The antenna box can send the response signal to the electronic box via a cable, such as a single coaxial cable, and conversion box for processing. In some embodiments, the electronic box is adapted to interface with a cable, such as a coaxial cable, and the antenna box sends the response signal to the electronic box via the cable without requiring a conversion box. The cable can be a single coaxial cable.

As stated above, the energizing signal may be a pre-set duration. A corresponding response signal from the implanted wireless may received in a window having a certain duration that depends, in part, on the duration of the energizing signal. In some embodiments, the end of the energizing signal and/or the response signal is used to control the electronic box, conversion box, and the antenna box. For example, the conversion box can detect the end of an energizing signal and change its mode of operation from transmitting the energizing signal to the antenna box to receiving a response signal from the antenna box. The antenna box may detect the end of the energizing signal and change its mode of operation from transmitting the energizing signal to the implanted sensor to receiving the response signal from the implanted sensor. After an end of a response signal, the antenna box and/or conversion box can change its mode of operation from receive to transmit in preparation for a subsequent energizing signal.

In some embodiments, the antenna box includes an amplifier that is adapted to amplify an energizing signal to a pre-set level before transmitting it to the implanted sensor via an antenna transmit element. The amplifier may provide a quick disconnect, or otherwise provide a gap in the transmit element, after transmitting the energizing signal to facilitate suppression of switching transients or residual energy that may reside in the transmit element and that can detrimentally affect operation of the system electronics. For example, the amplifier can provide a disconnect that is less than a certain amount of time, such as 100 nanoseconds, after the end of the energizing signal.

In some embodiments, an electronic box is provided that can communicate with the antenna box via a single cable such as a coaxial cable. For example, the electronic box may include certain functionality provided by a conversion box and does not require use of a conversion box in the communications system.

Wireless sensors, according to various embodiments of the present invention, may be any wireless sensor that can respond to an energizing signal within a pre-set frequency range with a response signal. The wireless sensor may be adapted to be implanted into an object. Examples of objects include humans, non-human animals, and inanimate objects. The wireless sensor may be adapted to change characteristics of its response signal based on conditions or characteristics of its environment or the object in which it is implanted. The response signal characteristics can be detected by certain communication systems according to various embodiments of the present invention to determine conditions or characteristics of the environment in which the wireless sensor is implanted.

Illustrative Antenna and Coaxial Cable

Figure 3:
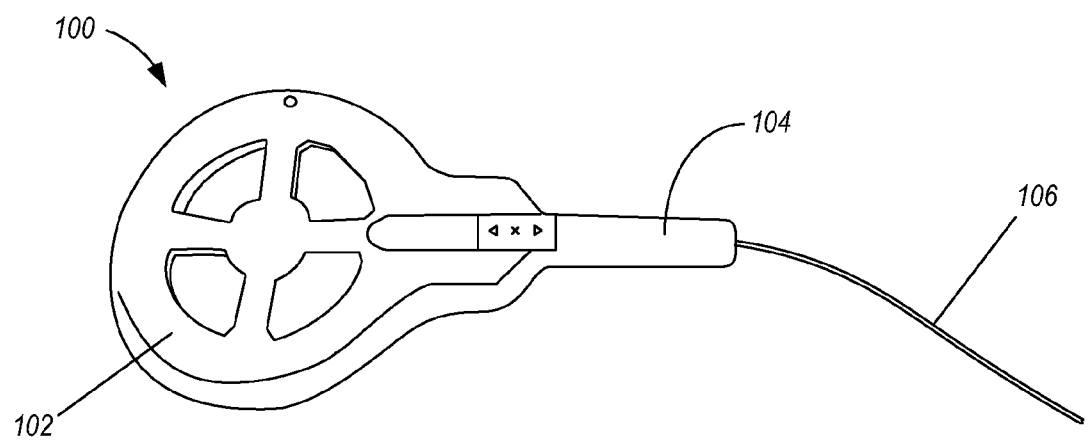
FIG. 3 illustrates an antenna and single cable according to one embodiment of the present invention.

Certain system circuitry according to some embodiments allow an antenna box to be connected via a cable, such as a single coaxial cable or single wire, to an electronic box, or to a conversion box that interfaces to an electronic box. In some embodiments, the conversion box may interface with the electronic box via a multiwire interface. FIG. 3 illustrates one embodiment of an antenna 100 that can be used to transmit signals to, and receive signals from, an implanted sensor in accordance with various aspects disclosed herein. The antenna 100 can include a coupling loop 102 and an antenna box 104 that includes circuitry to support signal transmission and reception. The coupling loop 102 can include a transmit element for transmitting signals onto a communication medium such as air and a receive element for recovering signals, such as a signal from an implanted wireless sensor that is responsive to an energizing signal, from a communication medium such as air. A cable 106, such as a single coaxial cable, can connect the antenna 100 to an electronic box (not shown) or a conversion box (not shown) that is connected to, or otherwise associated with, the electronic box. In some embodiments, a single coaxial cable having a length of ten feet and terminated with bayonent Neill-Concelman (BNC) connectors is used to connect the antenna 100 to a conversion box or electronic box. In other embodiments, the cable 106 is a bundled cable.

Illustrative Communication System

Communication systems according to various embodiments can be implemented using any components adapted to send and receive signals between an antenna and a conversion box or electronic box using a cable, such as a coaxial cable, that provides increased antenna movement. In some embodiments, an antenna box is connected to an electronic box via the coaxial cable. In other embodiments, the antenna box is connected to a conversion box via the coaxial cable and the conversion box is connected to the electronic box. For example, an existing electronic box that utilizes a multi-wire cable to transmit and receive various signals may be retrofitted by connecting it to a conversion box, in accordance with certain embodiments, to allow a single coaxial cable to allow communication between the electronic box and antenna box.

Figure 4:
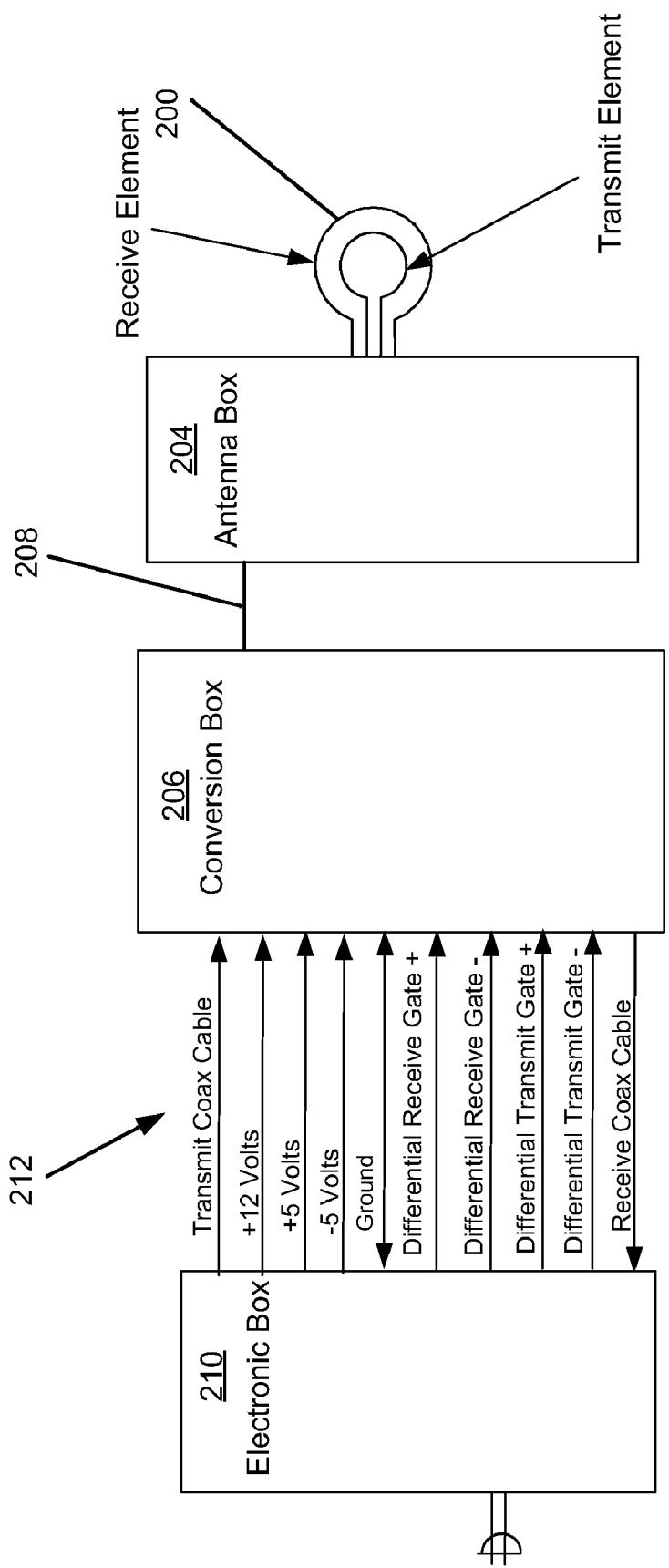
FIG. 4 is a block diagram of a communication system according to one embodiment of the present invention.

FIG. 4 is a block diagram representing one embodiment of such a system. An antenna 200 is associated with an antenna box 204. The antenna 200 may be any type of antenna that can transmit signals onto and recover signals from a communication medium such as air, or otherwise can communicate wirelessly with an implanted sensor. The antenna 200 in FIG. 4 includes a coupling loop that can include a receive element and a transmit element to provide for sufficient transmission and reception performance and response times during wireless communication with the implanted sensor. The antenna box 204 includes antenna box circuitry that can transmit and receive signals via antenna 200. The antenna box circuitry can provide amplification of an energizing signal and/or provide signal transmission and reception functions, such as timing control. In some embodiments, the antenna box 204 and antenna 200 are housed in a single unit. In other embodiments, the antenna box 204 and antenna 200 are housed in separated units that are connected via a cable or other type of connection.

The antenna box 204 can be connected to a conversion box 206 via a cable 208. The cable 208 may be a single coaxial cable, or any standard cable such as a Category 5 or Category 6, that can carry signals between the conversion box 206 and antenna box 204. The cable 208 may also carry power, such as a DC voltage, to the antenna box 204 and the antenna box circuitry. The cable 208 can be any length that allows the antenna 200 to be positioned as desired with minimal to no movement or placement limitations. In some embodiments, the cable 208 is ten feet or slightly less than ten feet long.

The conversion box 206 can be connected, attached, or otherwise associated with an electronic box 210 that provides energizing signal generation, response signal processing, and power. In some embodiments, the conversion box 206 is attached to the electronic box 210 using a connector such as a D-Sub connector manufactured by Amphenol Corp. of Wallingford, Conn. In other embodiments, the electronic box 210 includes the conversion box 206 or otherwise includes functionality provided by the conversion box. As described in more detail below, the conversion box 206 may include circuitry providing an interface between the electronic box 210 and antenna box 204. For example, the conversion box 206 may be adapted to communicate with the electronic box 210 by sending and receiving electronic box signals 212. The electronic box signals 212 can include a transmit signal, one or more DC voltages, ground, control signals, such as a pair of transmit gate signals and a pair of receive gate signals, and a receive signal.

The conversion box 206 can utilize all or some of the electronic box signals 212. For example, the conversion box 206 may utilize the transmit signals, receive signals, ground, at least one DC voltage signal, and receive gate signals, but not explicitly use transmit gate signals or additional DC voltage signals, to generate a complex multiplexed signal.

The electronic box 210 can generate an RF signal, such as an energizing signal, at a pre-set power level. An example of one such pre-set power level is 25 watts. The conversion box 206 can include an RF attenuator to decrease the power level of the energizing signal generated by the electronic box 210 to a lower level such as 250 milliwatts to support transmission of the energizing signal along the coaxial cable and minimize interference with other signals. The power amplifier included in the antenna box 204 can amplify the energizing signal to a pre-set level, such as 25 watts, before transmitting it onto a communication medium for reception by the implanted sensor. In some embodiments, the electronic box 210 may not amplify the energizing signal to a relatively high power level and can be connected to the antenna box 204 via a cable without using the conversion box 206 to attenuate the power level of the energizing signal.

Illustrative Electronic Box and Conversion Box

Figure 5:
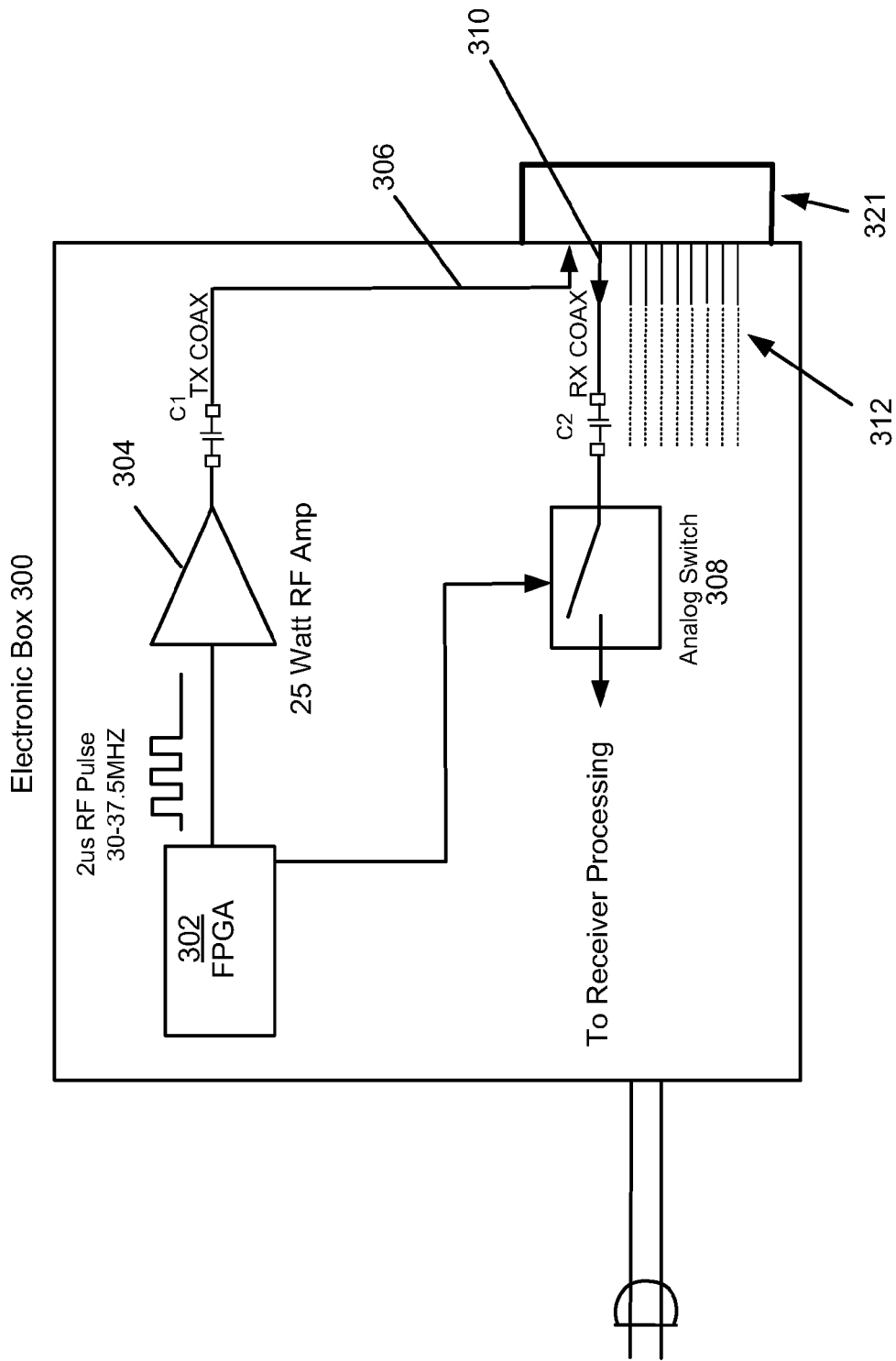
FIG. 5 is a block diagram of an electronic box according to one embodiment of the present invention.

Electronic boxes according to various embodiments may include circuitry adapted to generate an RF signal, such as an energizing signal, and process a response signal from an implanted wireless sensor. The electronic box may communicate with a conversion box or include circuitry for providing conversion box functions and communicate with the antenna box via a coaxial cable. FIG. 5 illustrates one embodiment of an electronic box 300 that can connect to a conversion box for implementation in a communications system. The electronic box 300 includes a field-programmable gate array (FPGA) 302 for generating an energizing signal. An example of an energizing signal is a two microsecond pulse at a frequency between 30 MHz and 37.5 MHz. A power amplifier 304 can amplify the transmitted energizing signal to a pre-set power level, such as 25 watts, and supply the amplified energizing signal to a transmit output 306. The FPGA 302 can also provide a control signal to a switch, such as analog switch 308. For example, the FPGA 302 can provide a control signal to the switch after the energizing signal burst ends, causing the switch to close and prepare the electronic box 300 circuitry for reception of a response signal. The analog switch 308 can be connected between a receiver input 310 and processing circuitry for processing the response signal. The electronic box 300 can also provide additional outputs 312, shown as dotted lines. The outputs 312 can include AC or DC power at one or more voltage levels and can include control signals for controlling transmit and receive functions.

Figure 6:
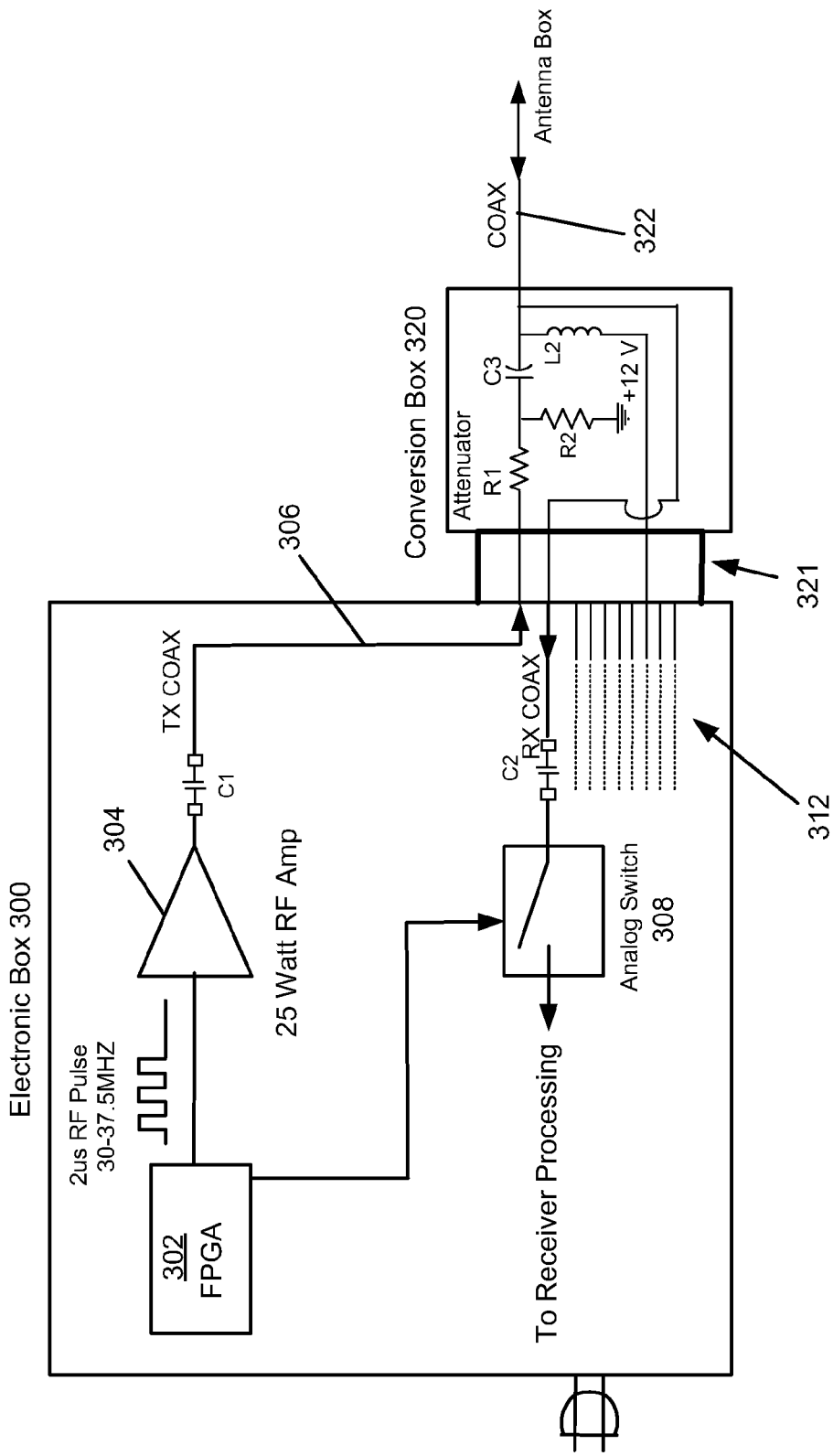
FIG. 6 is a block diagram of an electronic box associated with a conversion box according to one embodiment of the present invention.
Figure 7:
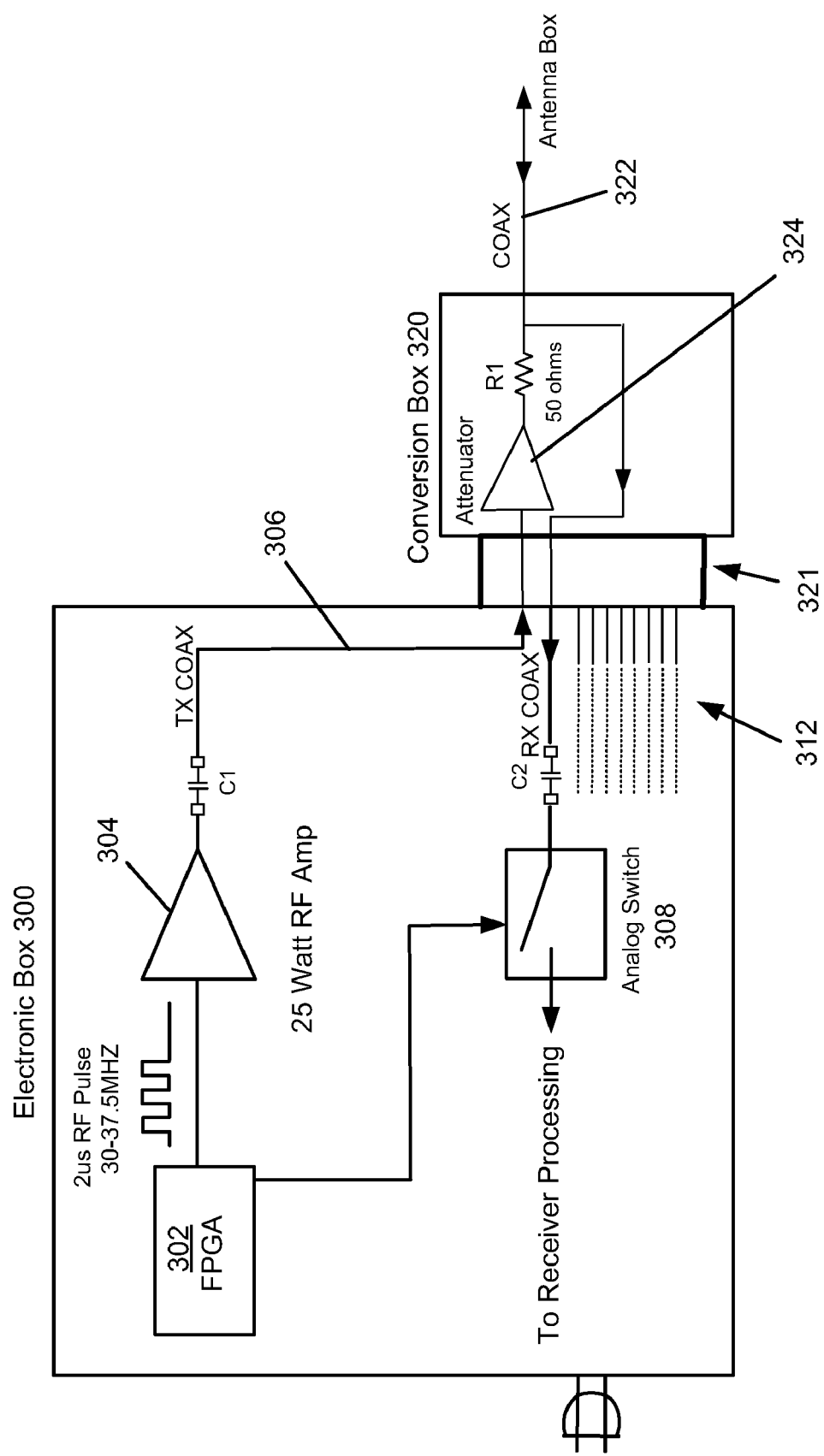
FIG. 7 is a block diagram of the electronic box and the conversion box of FIG. 6 with conversion box functional detail illustrated.
Figure 8:
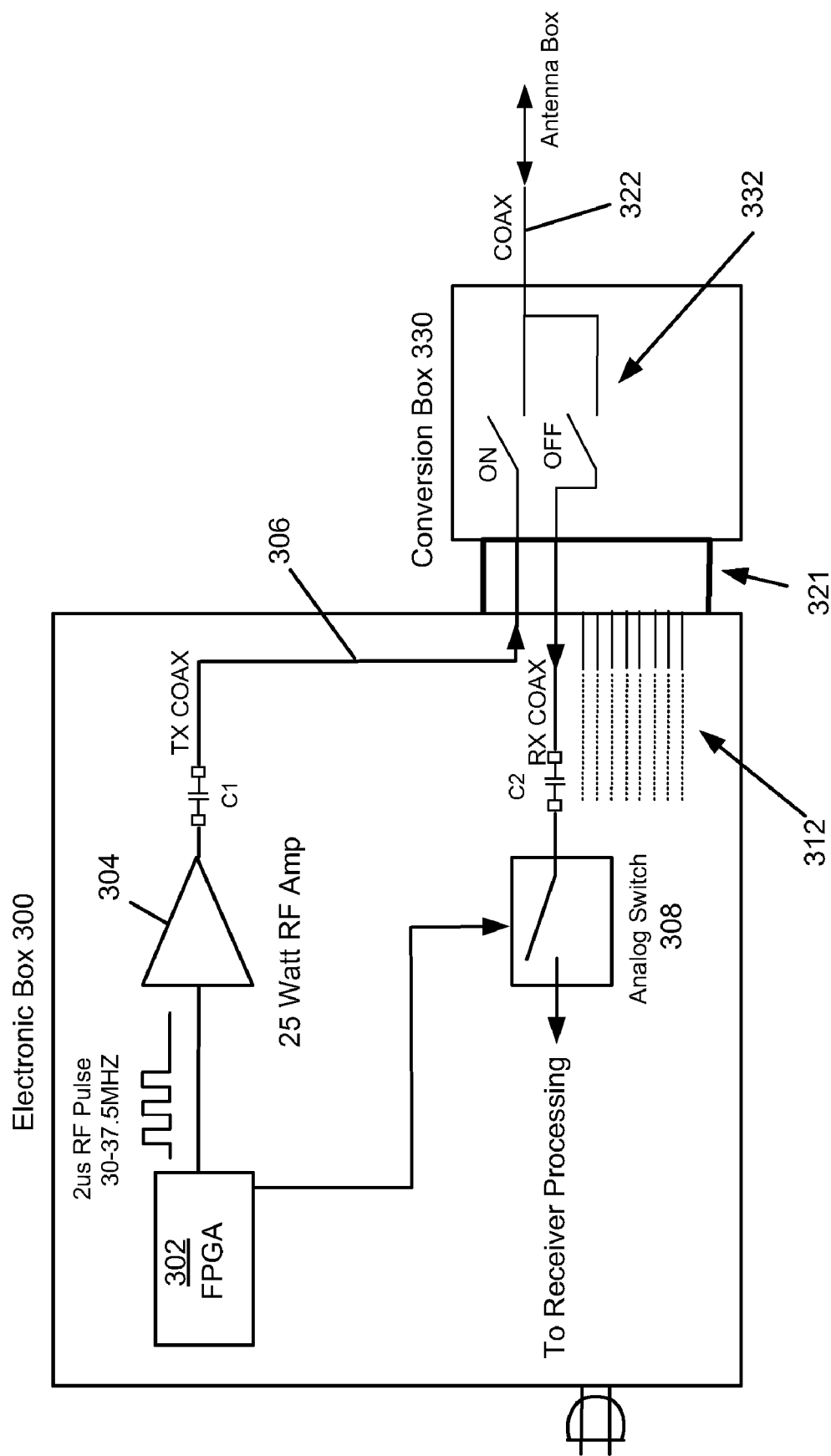
FIG. 8 is a block diagram of an electronic box associated with a conversion box according to a second embodiment of the present invention.

Electronic boxes, according to various embodiments of the present invention, that provide a relatively high-power signal output can be connected to any type of conversion box. In some embodiments, the conversion box is adapted to attenuate the power level of the energizing signal before providing the energizing signal to an antenna box via a cable. FIGS. 6-8 illustrate the electronic box 300 of FIG. 5 associated with certain embodiments of a conversion box. In FIG. 6, a conversion box 320 is connected to the electronic box 300 via a connector 321. The conversion box 320 includes circuitry that can attenuate the energizing signal to a lower power signal for sending it to the antenna box (not shown) via cable 322. In some embodiments, the conversion box circuitry includes an attenuator to reduce the power of the energizing signal to a lower level. In the circuitry shown in FIG. 6, inductor L2 and capacitor C3 form a diplex filter to combine an AC power of the energizing signal with a DC supply voltage that provides power to antenna box electronics. A low-power energizing signal may be useful for preventing a high power signal from being inadvertently received by the processing circuitry, preventing residual RF energy of the energizing signal from remaining in the coaxial cable, and/or preventing the destruction of receive electronics that may be sensitive and that are attached or associated with the coaxial cable.

FIG. 7 illustrates functionality provided by conversion box 320 of FIG. 6. An attenuator 324 is shown representing attenuator circuitry. In some embodiments, the attenuator 324 has a zero ohms output impedance, for example due to buffering, and the receiver portion of the electronic box 300 may have a relatively high input impedance. With this combination, impedance can be matched between the conversion box 320 and cable 322 by selecting source and termination resistances. In addition, the conversion box 320 can provide a DC voltage to the cable 322. Examples of a DC voltage include twelve volts.

FIG. 8 illustrates another embodiment of a conversion box 330. In addition to circuitry (not shown) for attenuating energizing signals, the conversion box 330 includes a switch 332 that can control the transmit operation mode or receive operation mode performed by the conversion box 330. In some embodiments, the switch 332 controls signal direction and the conversion box 330 does not include a feedback loop. The switch 332 can include one or more switches. For example, a transmit switch and a receive switch can be used by which the transmit switch is "on" when the receive switch is "off" and vice versa. The switch 332 can be controlled via control signals from the electronic box 300 or can be controlled by other conversion box circuitry. For example, the receive switch can be turned "on" upon detection of an end to the energizing signal, indicating an end to the transmit operation for a cycle.

Figure 9:
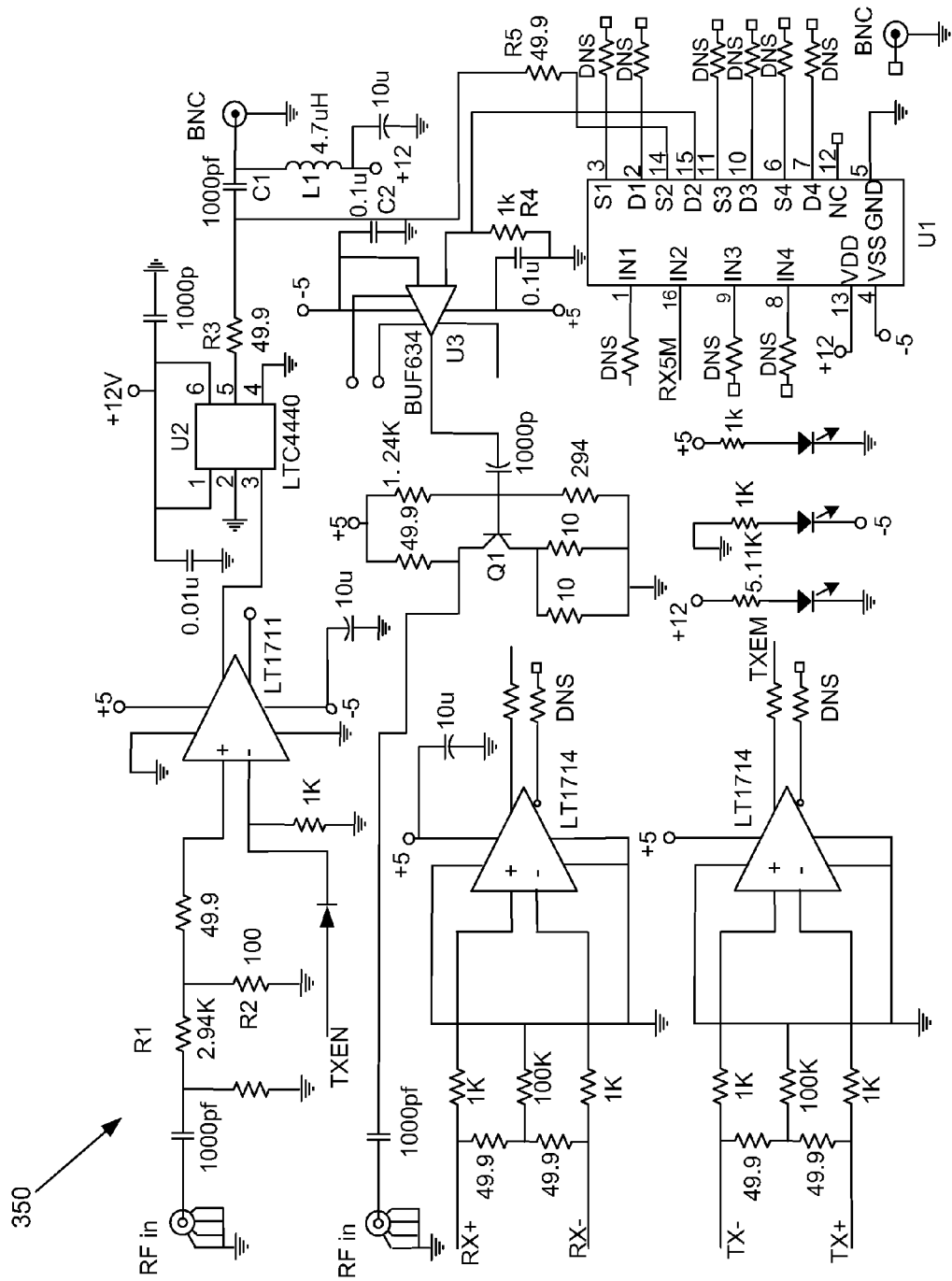
FIG. 9 schematically shows implementation details of a conversion box according to one embodiment of the present invention.

FIG. 9 schematically illustrates one embodiment of a conversion box 350 that can be implemented in communication systems in accordance with some embodiments of the present invention. The conversion box 350 can attenuate relatively high-power energizing signals received from an electronic box and otherwise can transmit and receive signals with an antenna box via a cable. R1 and R2, alone or in combination with other circuitry may attenuate an energizing signal from a relatively high power level to a relatively low power level. L1 and C1, alone or in combination with other circuitry, may provide diplex filtering. In some embodiments, an integrated circuit U1 that may include at least one analog switch, alone or in combination with other circuitry, and in particular pins 14 and 15, may provide switching capabilities. An example of U1 includes ADG1211 manufactured by Analog Devices Inc., Norwood Mass. R3, alone or in combination with other circuitry, may provide a desired impedance match between the conversion box 350 and cable during both transmission and reception operation.

In some embodiments, pin 5 of U2 is switched, during transmit operation, between ground and a DC voltage, such as twelve volts, at a selected rate that may depend on the resonant frequency, or expected resonant frequency, of the implanted sensor. Examples of the rate include a frequency between 30 MHz and 37.5 MHz. The twelve-volt RF pulse can be driven onto the cable through R3 to support retention of a selected driving impedance into the cable. An example of a selected driving impedance is 50 ohms.

In some embodiments, pin 5 of U2 is connected to zero volts or electrical ground during receive operation, causing the cable to be terminated to electrical ground. Such circuitry and operation of conversion box 350 can replace a need to switch operations as the same termination is used for both transmit and receive. A response signal that is received from the antenna box can be passed through U1, into a high impedance buffer U3, and amplified by Q1 before being received by electronic box processing circuitry. R3, alone or in combination with other circuitry, can maintain a correct impedance match without a requirement to switch the cable between a different source resistor or a different termination resistor. In some embodiments, impedance matching can be performed by R4, R3, and R5. An example of one impedance match is 47.636 ohms and a return loss of 32.32 dB. In addition, the output impedance of U2 and the impedance of L1, C1, and C2 may affect the impedance match and return loss.

Figure 10:
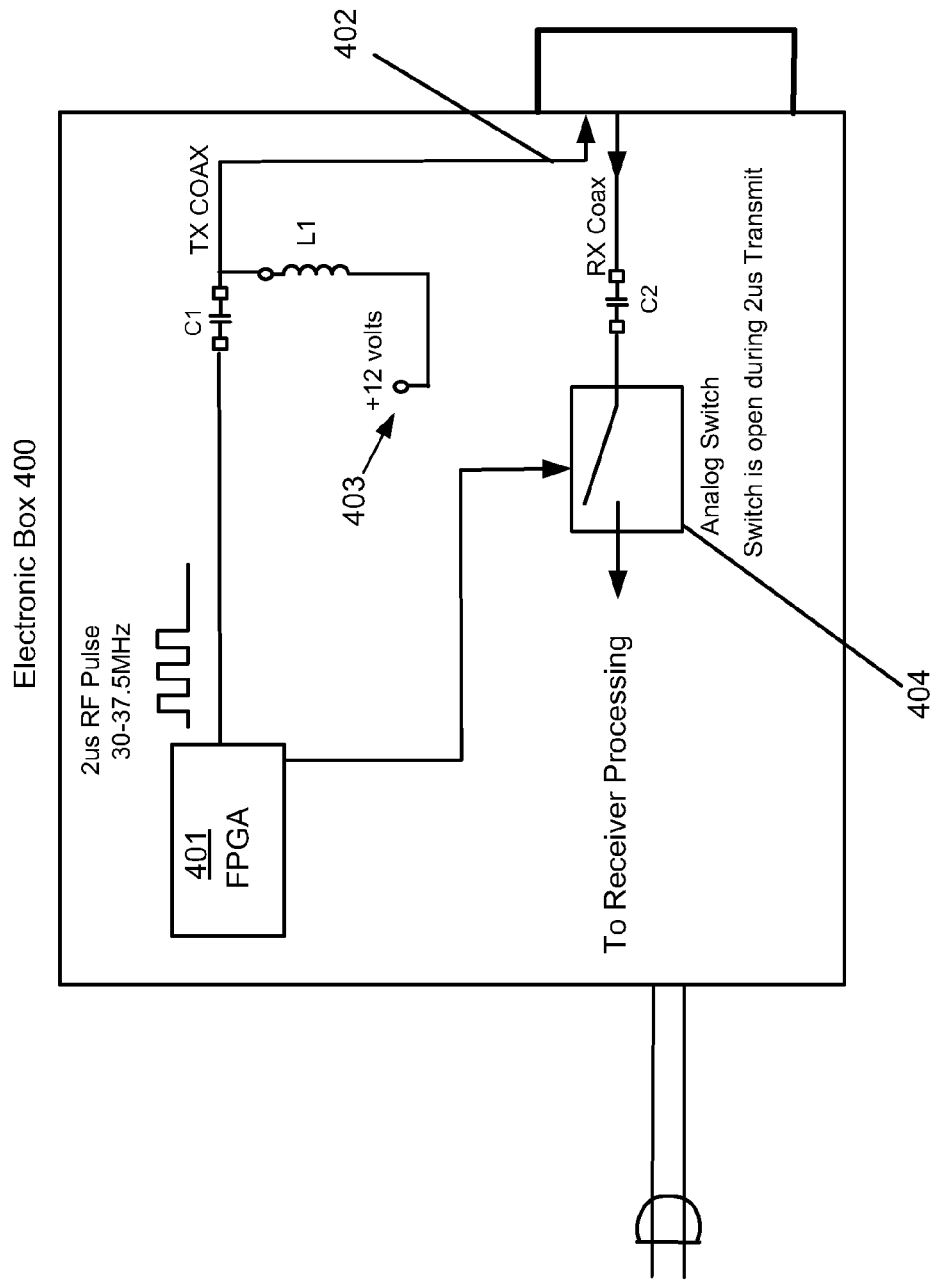
FIG. 10 is a block diagram of an electronic box according to a second embodiment of the present invention.

In some embodiments of the present invention, an electronic box can include certain features such that a conversion box is not required to provide an interface between the electronic box and an antenna box. FIG. 10 illustrates one embodiment of an electronic box 400 that can be implemented without requiring a conversion box. The electronic box 400 includes an FPGA 401 that can generate an RF signal, such as an energizing signal, at a pre-set frequency and at a pre-set duration. The generated energizing signal is provided as an output to a wire 402 along with a power signal, such as twelve volts DC power, from a power source 403. In some embodiments, the wire 402 is a single wire that can carry generated energizing signals and response signals between the electronic box 400 and an antenna box (not shown). For example, a response signal may be received by the electronic box 400 via wire 402. The FPGA 401 may be adapted to provide a control signal causing a switch, such as analog switch 404, to close when the FPGA 401 ends energizing signal generation and open during energizing signal generation and transmission. One function of the switch may include preventing the energizing signal generated by the FPGA 401 from being received by the circuitry for processing response signals. The energizing signal may be a relatively low power signal that does not need attenuation before it is provided to the antenna box.

Illustrative Cable

Cables according to various embodiments of the present invention may be any cable of any length capable of carrying power, energizing signals, and response signals between a conversion box (or electronic box) and an antenna box. An example of one cable is a coaxial cable that is ten feet long or slightly less than ten feet long. Since an RF signal travels approximately one foot per 1.5 nanoseconds, an energizing signal may traverse a cable that is approximately ten feet long in approximately 1.5 nanoseconds.

Cables according to certain embodiments of the present invention can be impedance matched to each of the connections with the conversion box (or electronic box) and the antenna box to provide desired performance. An example of one impedance match is 50 ohms. If the cable is not impedance matched, energy from RF signals, such as the energizing signal and/or response signal, may bounce back from one termination end to the other. Impedance matching can facilitate good return loss so that residual energy from the energizing signal and/or response signal dies down quickly before a next signal is carried by the cable. Low RF power for the energizing signal and/or response signal facilitates impedance matching by limiting the amount of residual power that may possibly remain in the cable. Conversion boxes (or electronic boxes) according to certain embodiments can generate or attenuate energizing signals to a relatively low RF power level and can include a power amplifier to prevent high power RF signals from being carried via the cable.

The following is a return loss calculation according to one embodiment of the present invention that illustrates the affect that impedance matching may have on the signals carried by coaxial cables according to various embodiments: Return loss (RL) on the conversion box side can be calculated as $$RL = 20 * \log\left(\frac{50 - 47.636}{50 + 47.636}\right) = 32.32 \text{ dB}$$

where 50 ohms is the characteristic impedance of the coaxial cable, and the coaxial cable is terminated in 47.636 ohms. A 32.32 dB return loss may result in $$\left(\frac{1}{10^{\frac{32.32}{10}}}\right),$$

or 0.058% of the power being reflected from the conversion (or electronic) box side of the coaxial cable termination. While an impedance termination calculation also can be performed on the antenna box end of the coax cable, such calculations may be optimistic. In practice, a 16 dB return loss can be achievable at each end of a ten-foot coaxial cable. A 16 dB return loss may be equivalent to 2.5% of the residual energy being reflected from each end of the coaxial cable approximately every 15 nanoseconds. The following table shows the residual energy in the coaxial cable for a 16 dB return loss on a ten foot long cable, and an initial power of 250 milliwatts:

TABLE 1

| Time | Residual Energy |
|---|---|
| 0 seconds | 0.25 watts |
| 15 nanoseconds | 0.0625 watts |
| 30 nanoseconds | 0.00015625 watts |
| 45 nanoseconds | 0.00000390625 watts |
| 60 nanoseconds | 0.00000009765625 watts |
| 75 nanoseconds | 0.0000000244140625 watts |
| 90 nanoseconds | 0.00000000006103515625 watts |
| 105 nanoseconds | 0.0000000000152587890625 watts |
| 120 nanoseconds | 0.000000000000003814697265625 watts |

After 120 nanoseconds, the residual energy in the coaxial cable, due to the original 250 milliwatts, is less than 0.04 picowatts and may be decreased as to not cause interference to the response signal.

In some embodiments of the present invention, the cable includes one coaxial cable, two coaxial cables, or a tapeworm cable. For example, one cable may be used to carry energizing signals and transmit signals, a second cable may carry test signals, a third cable may carry calibration signals, and a fourth cable may carry a power signal. In other embodiments, the antenna box communicates with the conversion box or electronic box wirelessly, without requiring a cable, but otherwise operating similarly.

Illustrative Antenna Box

Figure 11:
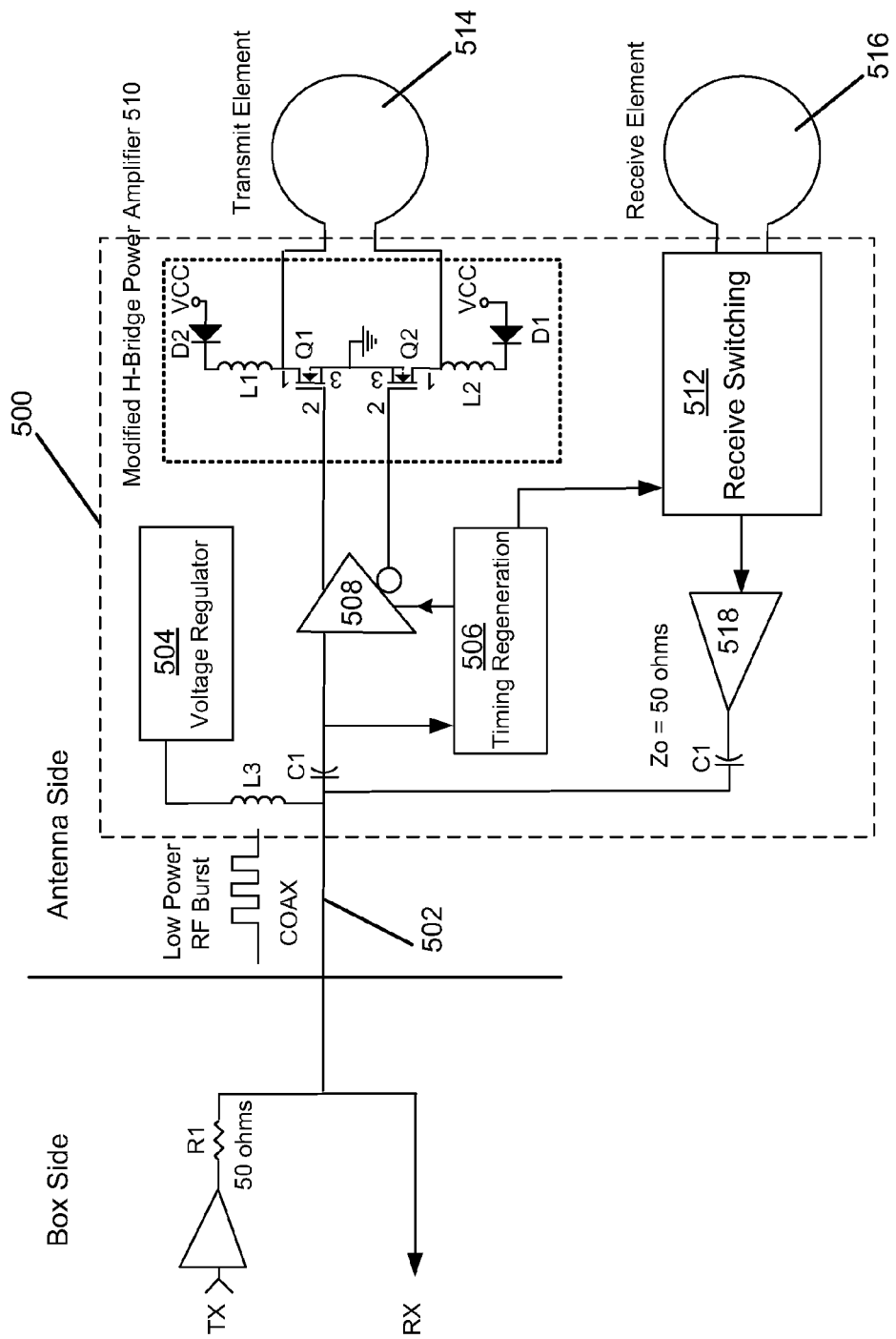
FIG. 11 is a block diagram of an antenna box connected to a conversion box or electronic box via a cable according to one embodiment of the present invention.

FIG. 11 illustrates one embodiment of an antenna box 500 that can receive an energizing signal, amplify the energizing signal to a desired RF power level, transmit the amplified energizing signal onto a communication medium such as air for reception by an implanted sensor, receive a response signal from the implanted signal, and provide the response signal to a conversion box (or electronic box) via a cable. The antenna box 500 is connected to a conversion box or electronic box (shown as "box side") via a cable 502. The antenna box 500 includes a voltage regulator 504 that receives power from cable 502 via L3. The voltage regulator 504 can regulate the DC voltage and, in some embodiments, provide DC power at two or more voltage levels to antenna box circuitry.

An energizing signal can be received by the antenna box 500 and can be provided to timing regeneration block 506 and a dual comparator 508. The dual comparator 508 can generate a differential drive to an RF amplifier that is a modified H-Bridge power amplifier 510 and otherwise provide the energizing signal to the modified H-Bridge power amplifier 510. The timing regeneration block 506 can include timing regeneration circuitry. The timing regeneration circuitry can detect the presence of an energizing signal and an end to the energizing signal, and output control signals to the dual comparator 508 and receive switch 512. For example, the timing regeneration block 506 may detect an end to the energizing signal and output a control signal to the dual comparator 508 to stop providing an input to the modified H-Bridge power amplifier 510 and to the receive switch 512 to switch "on" to receive a response signal.

The modified H-Bridge power amplifier 510 can amplify the energizing signal to a pre-selected level before the antenna wirelessly transmits the energizing signal to an implanted sensor. An example of a pre-selected amplification level includes 25 watts. The RF amplifier in FIG. 11 is a modified H-Bridge power amplifier 510. However, other types of RF amplifiers that can increase a power level of an RF signal and provide a disconnect mechanism from a transmit loop, such as transmit antenna element 514, at an end of the energizing signal can be used. The modified H-Bridge power amplifier 510 may provide a disconnect to the transmit loop within a certain amount of time, such as 100 nanoseconds, from the end of the energizing signal. A disconnect can include a gap in the transmit loop of a transmit antenna element to stop signal transmission onto the communication medium and decrease transient signals that may remain in the transmit loop as transmission ends. After amplification, the amplified energizing signal is provided to the transmit antenna element 514 for transmission onto a communication medium, such as air, and reception by an implanted sensor. The implanted sensor can respond to the energizing signal with a response signal that is received by a receive antenna element 516 associated with the antenna box 500. The response signal received by the receive antenna element 516 can be provided to an amplifier and buffer 518 through the receive switch 512 that has been switched "on" by the timing regeneration block 506. The amplifier and buffer 518 can amplify the weak response signal to a level acceptable for transmission to the box side via cable 502.

The amplifier and buffer 518 may also provide an output impedance to match the impedance of cable 502 or otherwise to facilitate efficient transmission along cable 502. In some embodiments, the amplifier and buffer 518 provides a 50-ohm output impedance for the termination end of cable 502 in antenna box 500. The response signal may be incidentally received by the dual comparator 508 and, in some cases, cause a false transmission to be detected during receive mode operation. The timing regeneration block 506 can disable the dual comparator 508 output based on its detection of an end to the energizing signal. For example, the timing regeneration block 506 can, after determining an end to the response time window, provide control signals to the dual comparator 508 to enable it to drive the modified H-Bridge power amplifier 510 and to turn the receive switch 512 "off" or to "open" it to prepare for another transmission period.

The timing regeneration block 506 can identify an end to the response signal after an end to a response time window. For example, the signal strength of the response signal may decrease over time. In some cases, the signal strength may exponentially decrease. A response time window can be used during which the response signal is received. The response time window can begin when the receive mode of the antenna box 500 begins and the response time window can end after a pre-set amount of time. An example of one pre-set amount of time is three microseconds.

Figure 12:
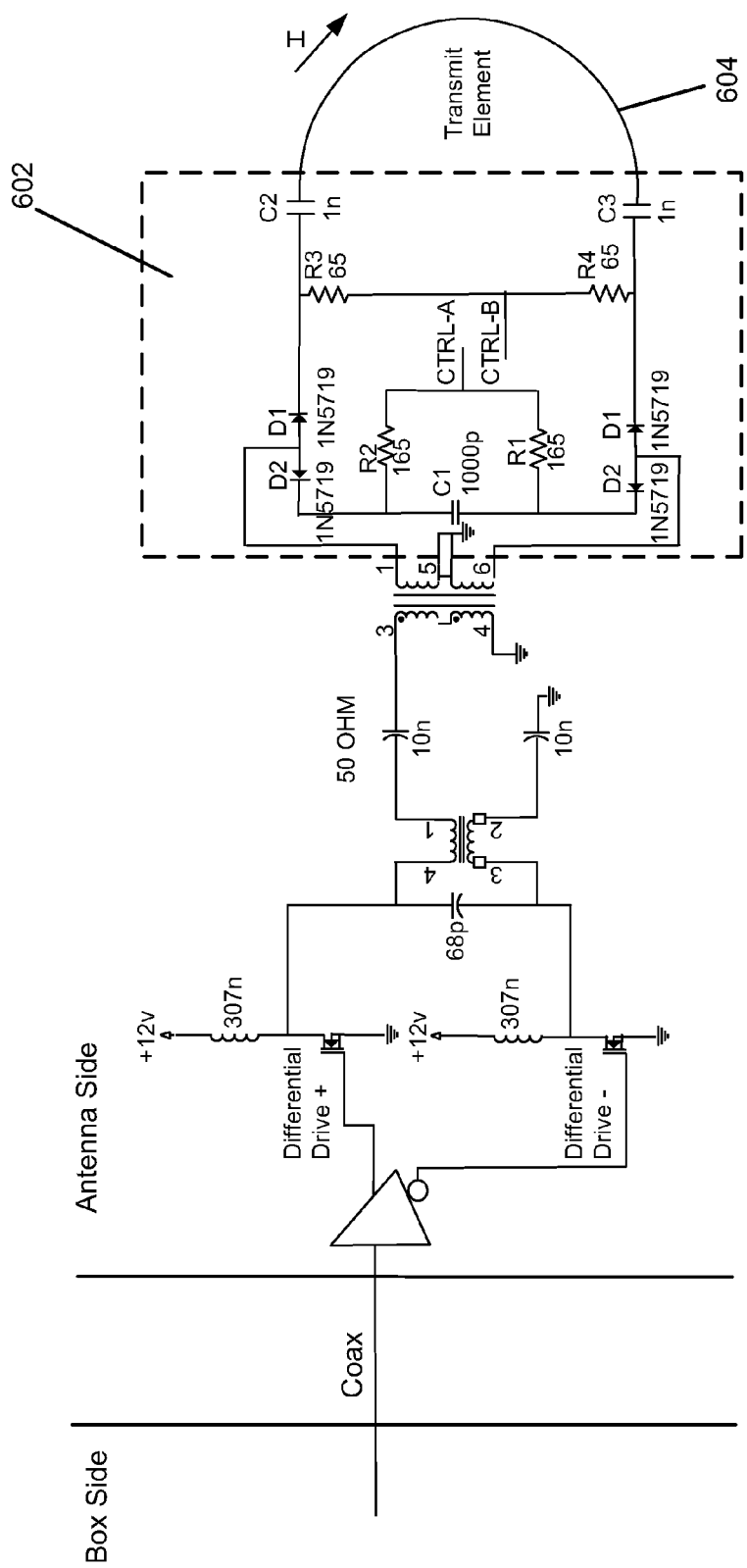
FIG. 12 schematically shows a transmit portion of an antenna box according to a second embodiment of the present invention.
Figure 13:
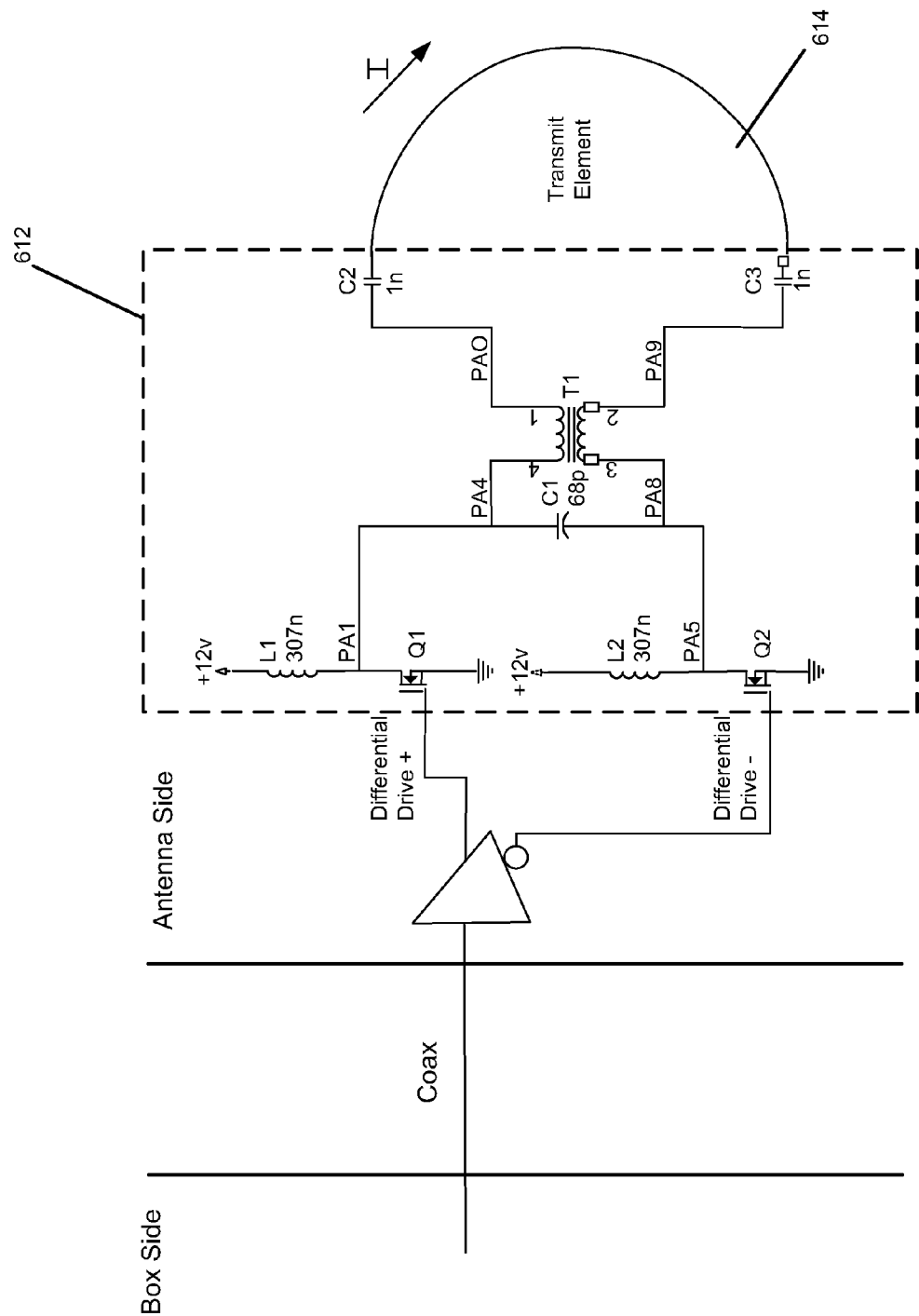
FIG. 13 schematically shows a transmit portion of an antenna box according to a third embodiment of the present invention.

FIGS. 12 and 13 illustrate additional embodiments of the transmission portions of an antenna box. In FIG. 12, an amplifier 602 includes diodes, such as pin switching diodes D1, D2, D3, and D4, that facilitate disconnection of the transmit loop at the end of the energizing signal. In FIG. 13, an amplifier 612 includes MOSFET transistors in a configuration that does not facilitate a disconnect of the transmit loop at the end of the energizing signal. In some instances, using an RF amplifier with pin switching diodes or with the H-Bridge MOSFET transistor configuration may reduce or eliminate residual RF energy remaining in associated transmit antenna elements, such as transmit element 614 in FIG. 13. Decreasing or eliminating residual RF energy can prevent residual energy from interfering with an antenna box's ability to receive response signals from an implanted sensor.

Figure 14:
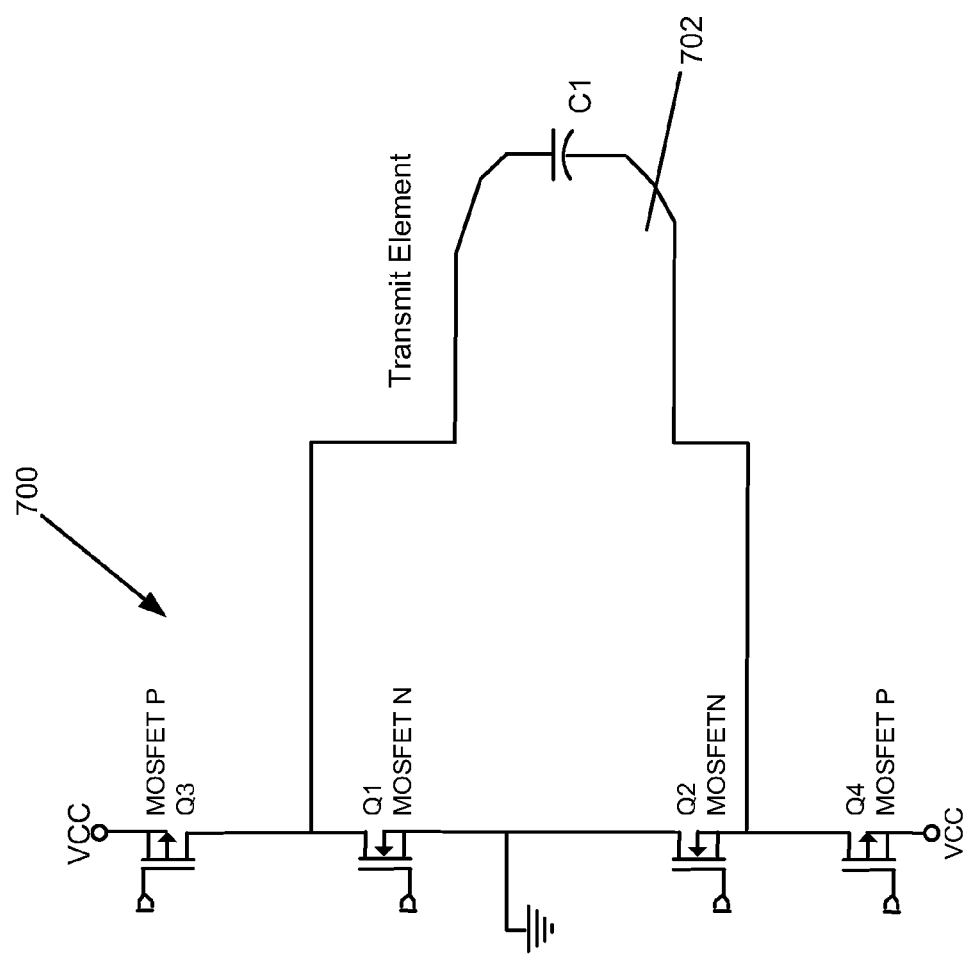
FIG. 14 schematically shows a full H-Bridge amplifier according to one embodiment of the present invention.

In some embodiments, the antenna box uses an H-Bridge RF power amplifier with additional MOSFET transistors to provide the desired disconnect performance. FIG. 14 illustrates one embodiment of an H-Bridge amplifier 700 and a transmit antenna element 702 that may be used in certain antenna box embodiments of the present invention as a power amplifier. The transmit antenna element 702 includes a capacitor C1 that is a tuning capacitor adapted to tune the transmit antenna element 702 to a desired resonant frequency. The H-Bridge amplifier 700 includes N-Channel MOSFET transistors Q1, Q2 and P-Channel MOSFET transistors Q3, Q4 that can turn "off" once transmission is complete and provide a disconnect break in the loop path, preventing residual energy from remaining in the transmit antenna element 702.

Figure 15:
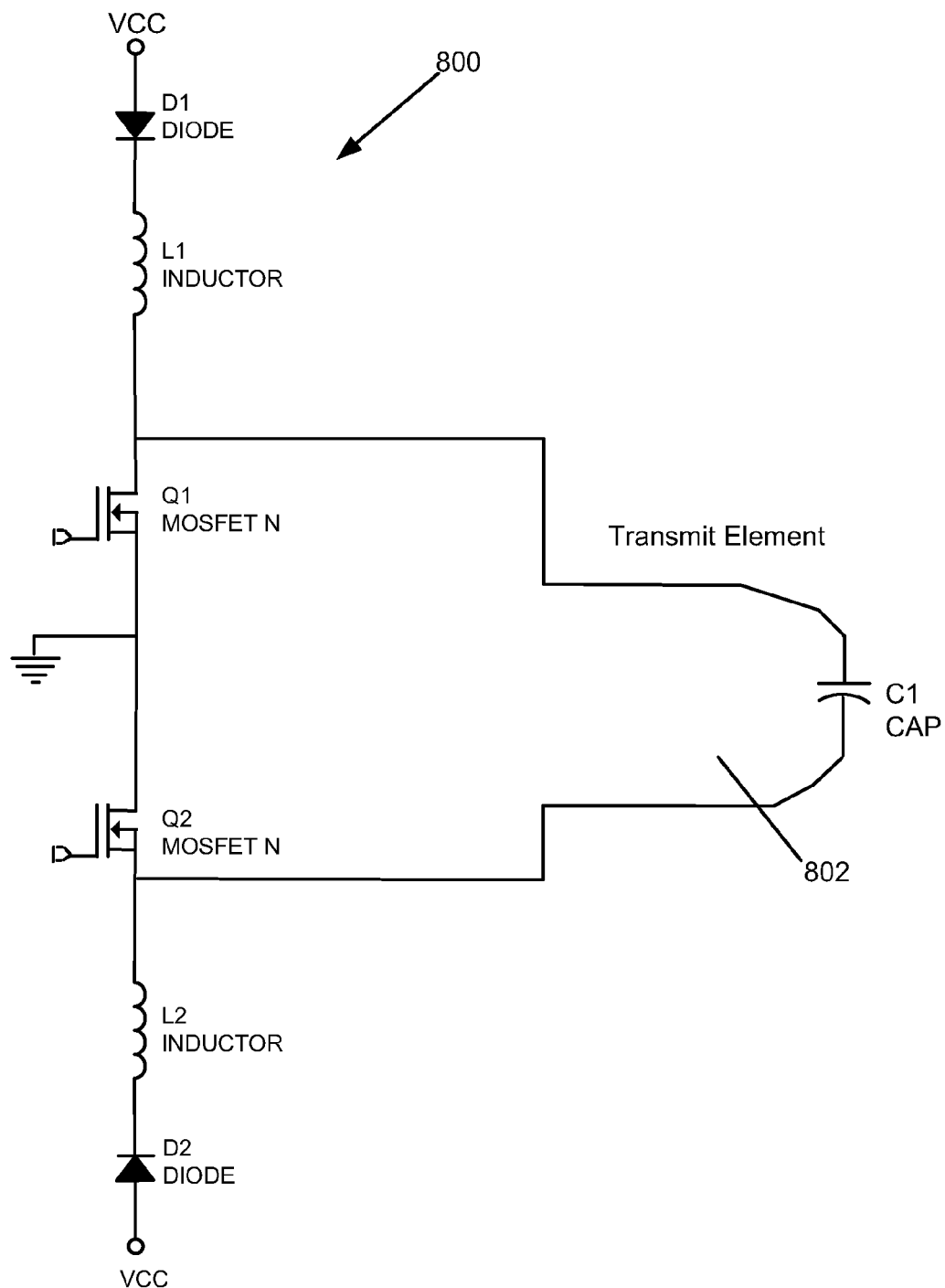
FIG. 15 schematically shows a modified H-bridge amplifier according to one embodiment of the present invention.

In some embodiments, a standard H-Bridge amplifier can be modified to provide amplification and disconnect capabilities for antenna box. FIG. 15 illustrates one embodiment of a modified H-Bridge amplifier 800 that can be implemented in certain embodiments of the invention. The modified H-Bridge amplifier 800 may require less space, consume less power, and provide an easier implementation than other amplifiers such as the standard H-Bridge amplifier. The modified H-Bridge amplifier 800 includes N-Channel MOSFET transistors Q1 and Q2, diodes D1 and D2, and inductors L1 and L2. The diodes D1 and D2 can cease conducting once the transistors Q1 and Q2 are disabled, providing a quick disconnect in a loop path and preventing residual energy from remaining in a transmit antenna element 802 that may interfere with antenna box receiving performance. For example, the modified H-Bridge amplifier 800 may provide a disconnect within a certain amount of time, such as 100 nanoseconds, after the end of the energizing signal. The modified H-Bridge amplifier 800 may be a lower cost amplifier solution that requires fewer components to turn "off" and is sized smaller then other amplifier designs. Furthermore, certain modified H-Bridge amplifier embodiments may improve transient or residual energy response of a transmit loop. For example, the modified H-Bridge may be adapted to decrease the effect switching transients have on system performance.

Antenna boxes according to certain embodiments of the present invention may include additional components that facilitate desired operation performance. For example, some antenna boxes may include a fan or other cooling device that are adapted to regulate temperature within the antenna box. Some circuitry components may be sensitive to temperature fluctuations and may not provide desired performance characteristics for receiving low power response signals if antenna box temperature varies. For example, the frequency or other signal characteristics of response signals may be inadvertently modified or obscured by circuitry operating at a temperature that varies from a normal operating range. A fan or other cooling device that can regulate temperature within the antenna box may prevent the temperature from varying. The fan or other cooling device may be powered by a power signal received from an electronic box over an antenna cable.

Figure 16:
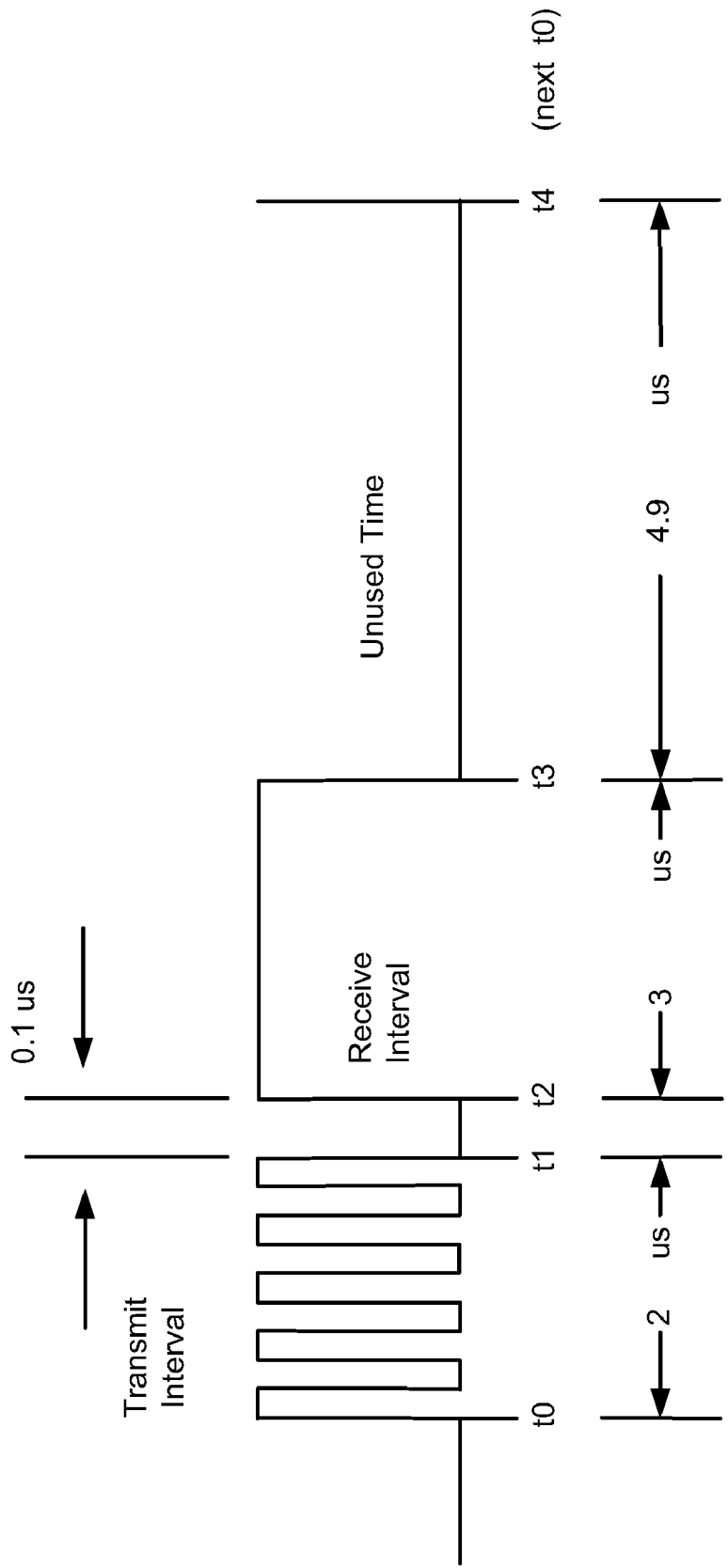
FIG. 16 illustrates signals with respect to time according to one embodiment of the present invention.

Certain embodiments of the present invention utilize timing constraints that can determine signal duration—energizing signal and/or response signal—and use such determination to control certain circuitry components. FIG. 16 illustrates an embodiment of an energizing signal and response signal with respect to time. A transmit interval is shown between t0 and t1 in which an energizing signal begins at t0 and ends at t1. The energizing signal includes a number of bursts or pulses. In some embodiments, the energizing signal includes a duration of 2 microseconds. The end of the energizing signal at t1 can be detected by certain antenna timing regeneration circuitry in some embodiments of the present invention to change its state and prepare for receiving a response signal beginning at t2. A transition time may be included between t1 and t2 to allow for cable reflections and other circuitry transients to decay. A disconnect mechanism of an antenna box amplifier, such as a standard H-Bridge or modified H-Bridge, can eliminate or decrease transients based at least in part on a rapid decay of the residual energy. In some embodiments, the transition time is 0.1 microseconds. The response signal begins at t2 and ends at t3. In some embodiments, the response signal duration is three microseconds. The end of the receive signal at t3 can be detected by certain circuitry to change the state from receive mode to transmit mode and prepare for a subsequent energizing signal, such as at t4. Unused time may be provided between t3 and t4 to allow for digital control signals for status, configuration, and to provide for other features.

The foregoing description of the embodiments of the invention has been presented only for the purpose of illustration and description and is not intended to be exhaustive or to limit the invention to the precise forms disclosed. Numerous modifications and adaptations are apparent to those skilled in the art without departing from the spirit and scope of the invention.

What is claimed is:

1. A system comprising:
a transmit antenna element for propagating an energizing signal onto a communication medium;
a receive antenna element for recovering an implanted sensor response signal from the communication medium, the implanted sensor response signal being responsive to the energizing signal; and
an antenna box in electrical communication with the transmit antenna element and with the receive antenna element, the antenna box comprising:
a power amplifier for amplifying the energizing signal received from an antenna cable to a second power level from a first power level and for providing the energizing signal at the second power level to the transmit antenna element; and
timing regeneration circuitry for outputting control signals to change the antenna box to a receive mode upon detecting an end to the energizing signal and to change the antenna box to a transmit mode upon identifying an end to the implanted sensor response signal by identifying an end to a response time window of a pre-set amount of time,
wherein the antenna box is capable of receiving the energizing signal from the antenna cable in the transmit mode and providing the implanted sensor response signal to the antenna cable in the receive mode.

2. The system of claim 1, wherein the antenna cable is one of:
a single coaxial cable; or
a bundled cable.

3. The system of claim 1, wherein the antenna box is capable of receiving the energizing signal and a power signal through the antenna cable from a conversion box in electrical communication with an electronic box capable of supplying the energizing signal and the power signal to the conversion box, the power signal being a direct current (DC) power signal.

4. The system of claim 3, wherein the antenna box further comprises a voltage regulator for regulating the DC power signal to supply a first DC power signal at a first voltage level and a second DC power signal at a second voltage level.

5. The system of claim 1, wherein the antenna box further comprises a receive switch controllable by the control signals outputted by the timing regeneration circuitry to change the antenna box to the receive mode or to the transmit mode.

6. The system of claim 1, wherein the power amplifier is an RF amplifier capable of providing a disconnect within a pre-set amount of time after the end of the energizing signal, the RF amplifier comprising at least one of:
a full H-Bridge amplifier; or
a modified H-Bridge amplifier.

7. The system of claim 6, wherein the pre-set amount of time after the end of the energizing signal is 100 nanoseconds.

8. The system of claim 1, wherein the antenna box further comprises a receive amplifier and buffer capable of amplifying the implanted sensor response signal to a response signal and capable of providing the response signal to an electronic box through the antenna cable.

9. A communication system comprising:
an electronic box for generating an energizing signal at a first power level;
a conversion box in electrical communication with the electronic box, the conversion box being capable of attenuating the energizing signal to a second power level and providing the energizing signal at the second power level to an antenna box through an antenna cable; and
the antenna box comprising:
a power amplifier for amplifying the energizing signal received from the conversion box through the antenna cable to a third power level from the second power level and for providing the energizing signal at the third power level to a transmit antenna element for transmitting the energizing signal at the third power level onto a communication medium; and
timing regeneration circuitry for outputting control signals to change the antenna box to a receive mode upon detecting an end to the energizing signal and to change the antenna box to a transmit mode upon identifying an end to an implanted sensor response signal by identifying an end to a response time window of a pre-set amount of time, the implanted sensor response signal being responsive to the energizing signal and recovered from the communication medium by a receive antenna element,
wherein the antenna box is capable of receiving the energizing signal from the conversion box through the antenna cable in the transmit mode and providing the implanted sensor response signal to the conversion box through the antenna cable in the receive mode.

10. The communication system of claim 9, wherein the conversion box comprises a diplex filter for combining the energizing signal with a direct current (DC) power signal received from the electronic box, the combined energizing signal and DC power signal being provided to the antenna box through the antenna cable.

11. The communication system of claim 9, wherein the electronic box comprises the conversion box.

12. The communication system of claim 9, wherein the electronic box comprises a field-programmable gate array (FPGA) for generating the energizing signal at a pre-selected frequency and for providing a control signal to a switch to toggle between a signal transmission mode and signal reception mode.

13. The communication system of claim 9, wherein the antenna cable is one of:
   a single coaxial cable; or
   a bundled cable.

14. The communication system of claim 9, wherein the power amplifier is an RF amplifier capable of providing a disconnect within a pre-set amount of time after the end of the energizing signal, the RF amplifier comprising at least one of:
   a full H-Bridge amplifier; or
   a modified H-Bridge amplifier.

15. The communication system of claim 14, wherein the pre-set amount of time after the end of the energizing signal is 100 nanoseconds.

16. The communication system of claim 9, wherein the antenna box further comprises a receive amplifier and buffer capable of amplifying the implanted sensor response signal to a response signal and capable of providing the response signal to the electronic box through the conversion box and the antenna cable, wherein the electronic box is capable of processing the response signal.

17. A method comprising:
   operating in a transmit mode by:
      receiving an energizing signal at a first power level from an antenna cable;
      amplifying the energizing signal to a second power level from the first power level;
      providing the energizing signal at the second power level to a transmit antenna element for propagating the energizing signal at the second power level onto a communication medium; and
      detecting an end to the energizing signal;
   changing to a receive mode from the transmit mode after detecting the end to the energizing signal;
   operating in the receive mode by:
      receiving an implanted sensor response signal recovered from the communication medium by a receive antenna element, the implanted sensor response signal being responsive to the energizing signal;
      providing the implanted sensor response signal to the electronic box through the antenna cable; and
      identifying an end to the implanted sensor response signal by identifying an end to a response time window of a pre-set amount of time; and
   changing to the transmit mode from the receive mode after identifying the end to the implanted sensor response signal.

18. The method of claim 17, further comprising:
   generating the energizing signal at a third power level;
   attenuating the energizing signal from the third power level to the first power level; and
   providing the energizing signal at the first power level to the antenna cable.

19. The method of claim 18, further comprising:
   amplifying the implanted sensor response signal to a fourth power level;
   providing the implanted sensor response signal at the fourth power level to the antenna cable; and
   processing the implanted sensor response signal at the fourth power level.

20. The method of claim 17, wherein operating in the transmit mode further comprises:
   providing a disconnect in the transmit antenna element within a pre-set amount of time after the end of the energizing signal.

* * * * *